United States Patent [19]

Fanelli et al.

[11] 4,214,087

[45] Jul. 22, 1980

[54] PRODUCTION OF CARBOXYLIC ACIDS FROM NITRILES

[75] Inventors: Anthony J. Fanelli, Rockaway; Abraham P. Gelbein, Plainfield, both of N.J.

[73] Assignee: The Lummus Company, Bloomfield, N.J.

[21] Appl. No.: 968,757

[22] Filed: Dec. 13, 1978

[51] Int. Cl.² ............... C07C 63/24; C07C 63/26; C07D 213/55
[52] U.S. Cl. ............... 546/319; 260/465 D; 562/484; 562/490; 562/493
[58] Field of Search ............... 562/484; 546/319

[56] References Cited

U.S. PATENT DOCUMENTS

| 3,492,345 | 1/1970 | Neugebauer et al. | 562/484 |
| 4,116,967 | 9/1978 | Gelbein et al. | 562/484 X |

*Primary Examiner*—Dolph H. Torrence
*Attorney, Agent, or Firm*—Louis E. Marn; Elliot M. Olstein

[57] ABSTRACT

A nitrile, such as terephthalonitrile or nicotinonitrile is hydrolyzed, in the vapor phase, in the presence of a solid acid catalyst, with ammonia which is evolved in the reaction and absorbed by the catalyst being stripped from the catalyst to reduce the production of intermediate amide products.

14 Claims, No Drawings

PRODUCTION OF CARBOXYLIC ACIDS FROM NITRILES

This invention relates to the production of carboxylic acids, and more particularly to the production of carboxylic acids from nitriles.

Aromatic or heterocyclic nitriles are generally converted to the corresponding carboxylic acid by aqueous hydrolysis which is catalized by an acid or base. Thus, for example, terephthalonitrile has been hydrolized with aqueous ammonia to produce the corresponding ammonium salt, which is then converted to the acid by steam stripping.

In U.S. application Ser. No. 877,339, filed on Feb. 13, 1978, which is a continuation of U.S. application Ser. No. 730,386, filed on Oct. 7, 1976 and now abandoned, there is disclosed an improved process for producing carboxylic acids from nitriles, wherein the nitrile is hydrolized in the vapor phase.

The present invention is directed to a further improvement in the process for producing carboxylic acids from nitriles, which employs vapor phase hydrolysis.

In accordance with the present invention, a nitrile and/or an intermediate hydrolysis product thereof is reacted with water, in the vapor phase, in the presence of an acid catalyst, in solid form, to convert the nitrile and/or intermediate hydrolysis product to the corresponding carboxylic acid, with ammonia which is evolved in the hydrolysis, and which is absorbed by the acid catalyst being stripped from the catalyst in order to minimize the production of intermediate amide product. Applicant has found that the acid catalyst absorbs ammonia generated in the reaction, with such ammonia absorption driving the reaction toward the product acid, and has further found that by stripping ammonia from the catalyst, the ammonia absorbing capacity of the catalyst is maintained to thereby increase the production of carboxylic acid product by minimizing the production of intermediate amide product.

The nitrile and water are reacted, in the vapor phase, at a temperature which is generally at least 200° F., and preferably at least 400° F. In general the temperature does not exceed 1000° F., and most generally does not exceed about 800° F. The temperatures which are employed are preferably above the dew point of both the feed and product components. The temperatures are most preferably selected to provide at least a 50% conversion of the nitrile at a contact or reaction time of no greater than 0.1 minute. It is to be understood that at the lower temperatures, in order to effect the hydrolysis in the vapor phase, it may be necessary to operate at a pressure which is less than atmospheric pressure.

The hydrolysis is preferably effected with steam to nitrile ratios in excess of stoichiometric ratios in that acid production is favored by increased steam partial pressure. The stoichiometric excess of water can be as much as to provide a steam to nitrile mol ratio of up to 500 to 1, with the steam to nitrile mol ratio generally being at least 5 to 1, and most generally at least 30 to 1. In most cases, the steam to nitrile mol ratio does not exceed about 100 to 1.

The total reaction pressure is generally selected to maintain the vapor phase conditions and the desired water partial pressure, with such total pressure generally being from 1 to 10 atmospheres.

The catalytic vapor phase reaction may be effected by any one of a wide variety of reaction techniques, including fixed bed, fluidized bed, dillute phase transport, etc., and the selection of a specific technique is deemed to be within the scope of those skilled in the art from the teachings herein.

In accordance with the present invention, acid production is increased by minimizing the production of amide intermediate product, with such a result being achieved by maintaining a low ammonia partial pressure in the reaction system. Applicant has found that the acid catalyst, in addition to providing its known catalytic function, absorbs ammonia evolved in the hydrolysis reaction, and in order to maintain the ammonia absorption capacity, which reduces ammonia partial pressure, it is necessary to strip absorbed ammonia from the catalyst. Thus, in accordance with the present invention, the ammonia absorbing capacity of the acid catalyst is maintained by stripping ammonia from the catalyst to thereby increase the product ratio of acid to amide.

The ammonia absorption capacity of the acid catalyst may be conveniently maintained by periodically subjecting the catalyst to an ammonia stripping operation. Ammonia may be stripped from the catalyst, for example, by contacting the catalyst with a suitable stripping gas, with such stripping preferably being effected at a temperature which is higher than the temperature employed for the hydrolysis procedure. Any one of a wide variety of stripping gases may be employed for effecting such ammonia stripping, and as representative examples of such gases there may be mentioned: steam, nitrogen, helium, and the like. The stripping may be effected by periodically or continuously withdrawing a portion of the catalyst from the hydrolysis reactor, followed by stripping of ammonia, and recycling of the stripped catalyst to the hydrolysis reactor. Alternatively, periodically, the feed to the hydrolysis reactor may be discontinued, and a stripping gas passed through the reactor to effect ammonia stripping, followed by continuation of the hydrolysis operation.

In employing a cyclic process for effecting hydrolysis and stripping, the amount of time that the catalyst is maintained on stream will vary with catalyst, reactants and conditions, and similarly, the amount of time for effecting the stripping portion of the cycle will vary with the amount of ammonia absorbed by the catalyst, and the hydrolysis on stream time. In general, the onstream cycle is for a period of from 4 to 9 min, and the stripping cycle is for a period of from 5 to 15 min. The stripping temperature generally reaches a temperature of at least 400° C., and in most cases, the stripping temperature need not exceed 475° C. It is to be understood that in effecting the stripping of ammonia from the catalyst, it is not necessary to strip all of the ammonia from the catalyst in order to maintain the ammonia absorption capacity of the catalyst. The selection of appropriate onstream and stripping cycles, as well as stripping conditions is deemed to be well within the scope of those skilled in the art from the teachings herein.

The use of an acid catalyst for effecting hydrolysis of nitriles to the corresponding carboxylic acid is generally known in the art, and as representative examples of acid catalysts which are employed in solid form in accordance with the teachings of the present invention, there may be mentioned: silica gel, silica-alumina, supported phosphoric acid, Group III metal phosphates and sulfates, e.g., phosphates and sulfates of aluminum, boron and gallium, transition metal oxides; e.g., one or more oxides of vanadium, chromium, manganese, iron, cobalt, nickel, etc. The catalysts are of the type employed for hydration, dehydration and esterification reactions. The preferred catalyst is supported phosphoric acid, preferably supported on silica-alumina.

The nitriles which are employed as starting materials for producing carboxylic acids in accordance with the present invention are either aromatic or heterocyclic nitriles. The aromatic nitriles contain one or more cyano-groups, preferably one or two cyano-groups and can be unsubstituted or substituted with other substituent groups; e.g., an alkyl group. The aromatic nucleus is preferably benzene or naphthalene. As representative examples, there may be mentioned: phthalonitrile, terephthalonitrile, isophthalonitrile, tolunitrile, 1-cyanonaphthalene, and 2,6-cyanonaphthalene. Similarly, the heterocyclic nitriles can contain one or more cyano-groups, with the heterocyclic nucleus generally being pyridine. The preferred starting materials are nicotinonitrile, isophthalonitrile, terephthalonitrile and phthalonitrile. As hereinabove noted, the starting material may be a nitrile intermediate hydrolysis product, such as the imides, amides, cyano-acids, cyanoamides and amide-acids, which can be employed alone or in combination with each other or the nitrile starting material.

The gaseous reaction effluent from the vapor phase hydrolysis contains the carboxylic acid, unreacted starting nitrile, ammonia, and some reaction intermediate, and the reaction product may be recovered by procedures generally known in the art. Thus, for example, in the production of terephthalic acid from terephthalonitrile, the reaction mixture can be cooled to condense the entire effluent and produce a water solution and slurry of the ammonium salts of terephthalic acid and intermediate hydrolysis product. The terephthalic acid and intermediate hydrolysis products can be separated from the ammonia by the addition of a suitable acid; for example, hydrochloric acid.

The separation may also be effected as described in U.S. application Ser. No. 730,385, filed Oct. 7, 1976.

The invention will be further described with respect to the following example; however, the scope of the invention is not to be limited thereby:

EXAMPLE 1

A solid phosphoric acid catalyst was prepared by impregnating crushed silica-alumina tablets (Grace 979) with 86% $H_3PO_4$. After drying overnight at 110° C., the catalyst gained 62% in weight. Fifty (50) mL of the catalyst was charged to a ¾" stainless steel tubular reactor and pretreated at 330° C. with a 3% $NH_3$ solution, for three hours, at a liquid flow rate of 0.1 mL/m. The catalyst was then alternated between feed and stripping cycles, as follows:

feed cycle: 23.8 min, 330° C., 15 psig, $H_2O$:TPN mol ratio fed=60, 163 $h^{-1}$ GHSV, downflow;
strip cycle: 11 min, 425° C., 15 psig, 286 mL $N_2$/min upflow.

Following three complete cycles, 0.55 g of product was isolated. Analysis by liquid chromatography indicated that the product was composed chiefly of terephthalic acid (TPA). at a ratio in excess of 50 to amide products, terephthalamic acid and terephthalamide. Minor amounts of cyanobenzoic acid (CBA) and unconverted terephthalonitrile (TPN), were also present. 10.63 mmol of $NH_3$ were removed during the stripping cycles.

EXAMPLE 2

Product analysis was carried out following six additional feed/stripping cycles. 1.33 g product was isolated, containing 87% TPA, 1.2% amide products, 4.4% CBA and 6% TPN (mol%). 13.9 mmol $NH_3$ were recovered from the stripping cycles.

EXAMPLE 3

The catalyst used in Example 2 was treated with 3% $NH_3$ solution at 330° C., at a liquid flow rate of 0.1 mL/min, to a level of saturation of the catalyst with $NH_3$. Four cycles were carried out. 0.61 g product was collected from 0.86 g TPN fed. Product composition amounted to 15.8% TPA, 1.11% combined terephthalamic acid/terephthalamide, 55.7% unconverted TPN and 27.0% CBA. 14.5 mmol $NH_3$ were recovered.

EXAMPLE 4

Following Example 3, four cycles were carried out, with the reactor temperature during the feed cycles at 348° C. 0.61 g product was recovered from 1.04 g TPN fed. The product consisted of TPA, at a ratio of >100 with respect to amides, plus negligible amounts of TPN and CBA. 4.28 mmol $NH_3$ were recovered from the stripping cycles.

EXAMPLE 5

TPN and steam in a ratio of 33 to 1 is passed over 50 gms. of phosphoric acid supported on silica-alumina at a temperature of 325° C., pressure of 15 psig and residence time of 20 seconds. The products were condensed and analyzed by liquid chromatography. The product ratio of TPA to amides was 7.9 and the TPN conversion was 69.3% (normalized).

The catalyst was then steam stripped at 325° C. for 130 min.; at 350° C. for 60 min.; and 375° C. for 120 min., with 17.8 mmol of ammonia being evolved. The hydrolysis was then repeated with a water to TPN mol ratio of 36 to 1. The ratio of TPA to amides in the product was 15.7 to 1 and the conversion was 78.5%.

The catalyst was then steam stripped at 346° C. for 120 min.; 400° C. for 100 min.; and 425° C. for 60 min., with 23.9 mmol of ammonia being evolved. The hydrolysis was repeated at 325° C. with a steam to TPN mol ratio of 45.6 to 1. The product had a TPA to amide ratio of greater than 75, and the TPN conversion was greater than 95%.

The present invention is particularly advantageous in that nitrile is converted to acid in shorter reaction times, at lower pressures, and at increased acid to amide by-product ratios.

Numerous modifications and variations of the present invention are possible in light of the above teachings and, therefore, within the scope of the appended claims, the invention may be practiced otherwise than as particularly described.

We claim:
1. In a process for hydrolizing a nitrile to the corresponding carboxylic acid, the improvement comprising:
effecting said hydrolysis by reacting steam and a nitrile selected from the group consisting of (1) pyridine substituted with from 1 to 2 cyano groups and (2) aromatic nitriles having from 1 to 2 cyano groups substituted on an aromatic nucleus selected from the group consisting of benzene and naphtha- lene, and intermediate hydrolysis products of (1) and (2), in the vapor phase, in the presence of an acid catalyst in solid form selected from the group consisting of silica gel, silica-alumina, supported phosphoric acid, group III metal phosphates, Group III metal sulfates and transition metal oxides at a temperature which is above the dew point of both the nitrile and corresponding carboxylic acid; and stripping ammonia evolved in said hydrolysis and absorbed by the catalyst from said catalyst to increase the product ratio of carboxylic acid product to amide byproduct.

2. The process of claim 1 wherein the acid catalyst is subjected to alternate hydrolysis and stripping cycles.

3. The process of claim 2 wherein the hydrolysis cycle is for a period of from 4 to 9 minutes and the stripping cycle is for a period of from 5 to 15 minutes.

4. The process of claim 3 wherein the stripping is at a temperature of at least 400° C.

5. The process of claim 2 wherein the ammonia is stripped from the catalyst by use of a stripping gas.

6. The process of claim 2 wherein the catalyst is supported phosphoric acid.

7. The process of claim 6 wherein the nitrile is terephthalonitrile.

8. The process of claim 6 wherein the nitrile is isophthalonitrile.

9. The process of claim 6 wherein the nitrile is nicotinonitrile.

10. The process of claim 1 wherein the steam to nitrile mol ratio is at least 30:1.

11. The process of claim 10 wherein the catalyst is supported phosphoric acid.

12. The process of claim 11 wherein the nitrile is terephthalonitirle.

13. The process of claim 11, wherein the nitrile is isophthalonitirle.

14. The process of claim 11 wherein the nitrile is nicotinonitrile.

* * * * *